United States Patent [19]

Silvermetz et al.

[11] 4,299,114
[45] Nov. 10, 1981

[54] METHOD OF TESTING THE INTEGRITY OF AN ULTRASONIC SYSTEM FOR SENSING LIQUID-FLUID INTERFACES

[75] Inventors: David Silvermetz, Wantagh; George L. Adams, Bayshore, both of N.Y.

[73] Assignee: Envirotech Corporation, Menlo Park, Calif.

[21] Appl. No.: 158,109

[22] Filed: Jun. 10, 1980

[51] Int. Cl.³ .................. G01F 25/00; G01N 29/00
[52] U.S. Cl. ........................... 73/1 H; 73/1 DV; 73/290 V; 324/80
[58] Field of Search .................. 73/1 H, 1 DV, 290 V

[56] References Cited

U.S. PATENT DOCUMENTS

| | | | |
|---|---|---|---|
| 3,213,438 | 10/1965 | Felice et al. | 73/290 V |
| 3,520,186 | 7/1970 | Adams et al. | 73/290 V |
| 3,851,333 | 11/1974 | Fishman | 73/290 V X |
| 4,118,983 | 10/1978 | Brazhnikov | 73/290 V |
| 4,182,155 | 1/1980 | Fowler | 73/1 DV |

FOREIGN PATENT DOCUMENTS 256300  11/1969  U.S.S.R. .................. 73/1 H

*Primary Examiner*—Daniel M. Yasich

*Attorney, Agent, or Firm*—Robert E. Krebs; Thomas J. McNaughton

[57] ABSTRACT

An ultrasonic system for sensing a liquid-fluid interface comprises a support structure (10) to which a transmitting crystal (21) and a receiving crystal (22) are bonded in such a way that the crystals (21 and 22) are positioned opposite each other across a gap (30). Each of the crystals (21 and 22) has a relatively high resonant frequency and a relatively low resonant frequency. An amplifier means (40) and a bandpass filter means (50) are connected to the crystals (21 and 22) to form a feedback loop. In normal operation, the transmitting crystal (21) is excited to resonate at its high resonant frequency in order to cause transmission of an ultrasonic signal across the gap (30) without causing appreciable ultrasonic transmission through the support structure (10) to the receiving crystal (22). When it is desired to test the system for integrity in the absence of liquid in the gap (30), the transmitting crystal (21) is excited to resonate at its low resonant frequency and the passband of the bandpass filter means (50) is shifted to enable low frequency oscillations to occur in the feedback loop due to ultrasonic transmission (i.e., cross-talk) through the support structure (10) between the crystals (21 and 22).

10 Claims, 1 Drawing Figure

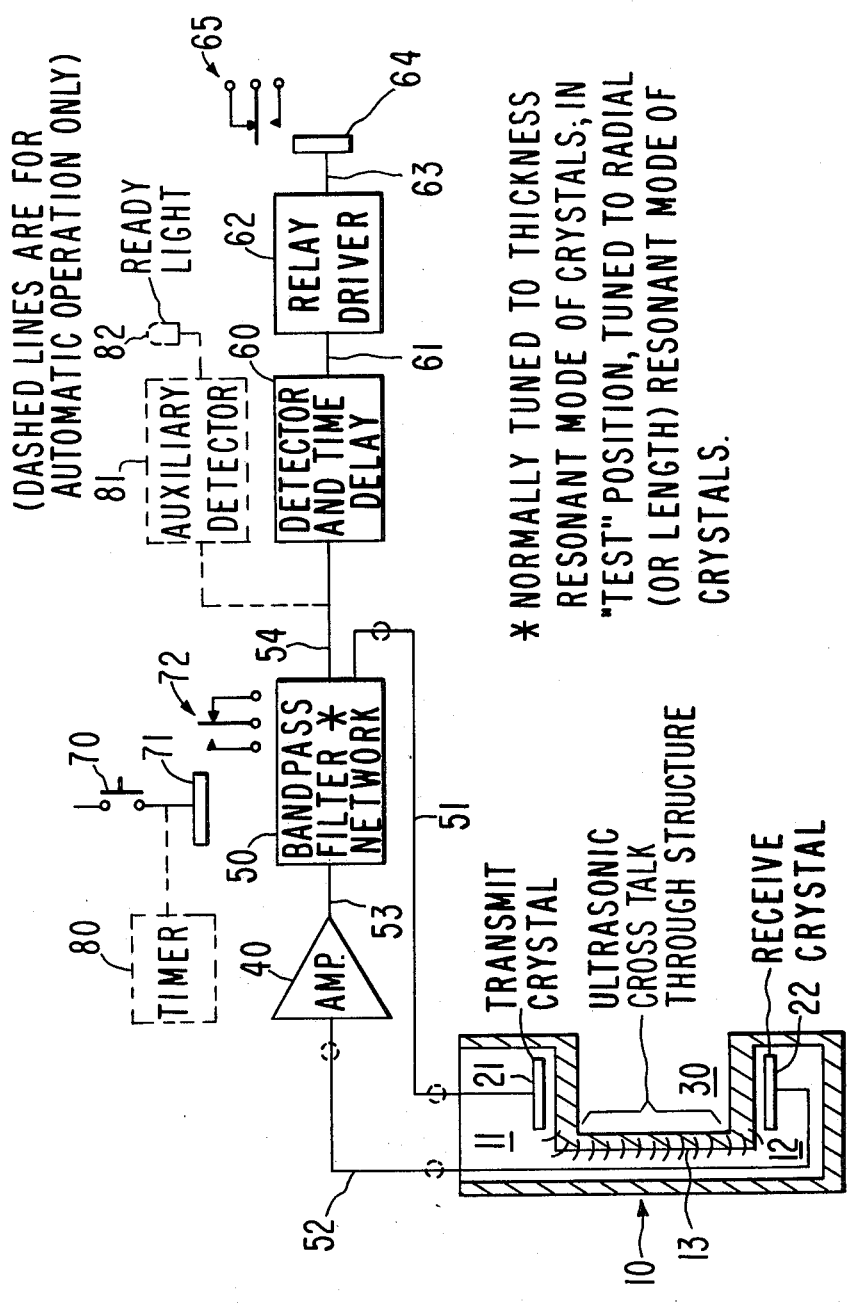

METHOD OF TESTING THE INTEGRITY OF AN ULTRASONIC SYSTEM FOR SENSING LIQUID-FLUID INTERFACES

BACKGROUND OF THE INVENTION

1. Field of the Invention

This invention provides a method of testing the integrity of an ultrasonic system for sensing liquid-fluid interfaces.

2. State of the Art

According to the prior art, a typical ultrasonic system for sensing a liquid level, or more generally for sensing a liquid-fluid interface, comprises means for continuously transmitting an ultrasonic signal of at least 500 kilohertz, means for receiving the transmitted ultrasonic signal, and means for detecting the received signal. Typically, the detecting means is connected to means for operating a valve, pump or servomechanism.

In a typical liquid-fluid interface sensing system of the prior art, a transmitting transducer and a receiving transducer are disposed to provide a straight-line ultrasonic signal path that intersects the liquid-fluid interface at an angle of incidence of from 0° to 90°. The transmitting and receiving transducers comprise piezoelectric crystals that are interchangeably or mutually positioned about (e.g., above or below) a desired liquid interface level in a detection area. Usually, one crystal is positioned above the desired interface level, and the other crystal is positioned below the desired interface level. However, in particular embodiments, both crystals may be positioned on the same side of the interface.

It is convenient to discuss the prior art and also the present invention in terms of a liquid-gas (or more usually, a liquid-air) interface. However, the "fluid" of the generalized liquid-fluid interface could also be a liquid. Thus, the interface to be detected could be the interface between two different liquids such as water and oil, or a slurry and water.

In operation, an electronic control unit generates an electrical signal, which is converted to an ultrasonic signal at the transmitting transducer. As long as the liquid-fluid interface stays within the gap between the transmitting and receiving transducer crystals, at least a portion of the path traversed by the ultrasonic signal in crossing the gap is through the liquid. After passing through the liquid, the ultrasonic signal is reconverted to an electrical signal at the receiving transducer. The reconverted electrical signal is then amplified to produce an output signal that can be used, e.g., to energize a relay for controlling a servomechanism. However, when the liquid-fluid interface falls below the gap between the transducers, the ultrasonic signal crossing the gap becomes so attenuated that the relay cannot be energized.

In a typical liquid-fluid interface sensing system of the prior art, the transmitting and receiving crystals are supported in a container or receptacle for the liquid to be detected, and associated electronic circuitry is adjusted so that when the level of the liquid to be detected (or more generally, the liquid-fluid interface) reaches the level of the gap between the crystals, ultrasonic transmission through the gap occurs at sufficient strength to maintain self-sustained oscillations in a closed electronic/ultrasonic feedback loop. In the absence of detectable liquid in the gap, however, the system remains in a quiescent non-oscillating state.

In many applications, it is desirable to be able to check the integrity of an interface sensing system of the above-described type before the level of the liquid to be detected reaches the level of the gap between the transmitting and receiving transducers. However, the output signal generated by such a system is typically the same (i.e., a NULL signal) when the level of the liquid to be detected moves away from the gap as when a defect has occurred in a portion of the electronics or in a transducer, or when a transducer cable has been cut or disconnected. Thus, until the present invention it has not generally been possible to test the integrity of an ultrasonic liquid-fluid interface sensing system, where the system is in place for sensing a liquid-fluid interface that has not yet reached the level of the gap between the transducers.

Attempts have been made in the prior art to provide system integrity checks for ultrasonic liquid level detectors. For example, U.S. Pat. No. 3,851,333 discloses an ultrasonic liquid level detector that utilizes a spray adaptor and pump means for creating an environment that simulates operational conditions. However, until the present invention, in-place testing of the integrity of an ultrasonic liquid-fluid interface sensing system such as that described in U.S. Pat. No. 3,520,186 has not been possible.

SUMMARY OF THE INVENTION

The present invention provides a method and associated electronic circuitry for testing the integrity of an ultrasonic liquid-fluid interface sensing system of the type described in U.S. Pat. No. 3,520,186. According to the present invention, integrity testing is accomplished by detecting the transmission of ultrasonic cross-talk through a support structure for transmitting and receiving transducers of the system when the transducers are operated in a low-frequency resonant mode.

With reference to the interface sensing system described in U.S. Pat. No. 3,520,186, it has been found that ultrasonic cross-talk through a cross member of a transducer support structure is often as much as ten times greater when the transducer crystals are caused to resonate in a low-frequency lateral (or "radial") mode than in a high-frequency longitudinal (or "thickness") mode. The system normally operates in the longitudinal or "thickness" mode in order to minimize cross-talk through the support structure. The present invention, however, makes use of this cross-talk effect by allowing the transmitting transducer crystal to oscillate in the lateral or "radial" resonant mode during the integrity test procedure.

When an integrity test procedure according to the present invention is to be initiated, a frequency passband in a feedback loop that includes the two transducers is shifted down so that the lower frequency resonant mode of the transmitting transducer crystal (in particular, the lateral or "radial" mode) lies within the passband. Oscillations in the feedback loop at the lower resonant frequency due to cross-talk through the transducer support structure are then detected, and a signal is generated indicating that the system is operational.

DESCRIPTION OF THE DRAWING

The drawing FIGURE is a block diagram showing electronic circuitry for implementing the integrity testing method of the present invention.

DESCRIPTION OF THE PREFERRED EMBODIMENT

The method of the present invention is intended primarily for use in testing the integrity of a liquid level or liquid-fluid interface sensing system of the type disclosed in U.S. Pat. No. 3,520,186. Accordingly, U.S. Pat. No. 3,520,186 is incorporated herein by reference.

As shown schematically in the drawing, a liquid-fluid interface sensing system of the type disclosed in U.S. Pat. No. 3,520,186 comprises a housing structure 10, which is preferably fabricated from stainless steel into a hollow C-shaped configuration. The housing structure 10 has a first end arm 11 and a second end arm 12, which are connected by a cross member 13.

A transmitting transducer comprising a first crystal 21 is mounted inside the first end arm 11, and a receiving transducer comprising a second crystal 22 is mounted inside the second end arm 12. The crystals 21 and 22 are of the piezoelectric type (typically of barium titanate, lead zirconate or lead metaniobate), and are generally configured as discs. Each of the crystals 21 and 22 is configured to have a resonant frequency above 500 kilohertz in a longitudinal or "thickness" dimension, and a much lower resonant frequency (i.e., 100 to 300 kilohertz) in a lateral or "radial" dimension.

The crystals 21 and 22 are positioned opposite each other across a gap 30 between the end arms 11 and 12 of the housing structure 10. The crystals 21 and 22 are mounted in the housing structure 10 in a way that minimizes transmission of ultrasonic signals through the cross member 13 when the crystals 21 and 22 are operating in their longitudinal or "thickness" resonant mode, yet optimizes transmission of ultrasonic signals across the gap 30. Ultrasonic transmission through the cross member 13, known as "cross-talk", would interfere with the detection of ultrasonic signals transmitted across the gap 30. Acoustical isolation of the crystals 21 and 22 from the walls of the housing structure 10 can be provided by conventional means such as by supporting the crystals 21 and 22 on rubber feet that are secured to the interior walls of the first and second end arms 11 and 12, respectively, by an epoxy resin. Epoxy resin or a plastic, glass or ceramic material may be packed into the hollow housing structure 10 around the crystals 21 and 22 in order to retain the crystals 21 and 22 so that their lateral extensions are substantially parallel to each other.

Electronic circuitry, which includes components represented schematically by an amplifier 40 and a bandpass filter network 50, is provided to establish an electronic/ultrasonic feedback loop with the crystals 21 and 22. Particular details for such circuitry could readily be devised by a worker skilled in the art. In particular, the circuit details described in U.S. Pat. No. 3,520,186 could be used for such a feedback loop.

As shown in the drawing, the transmitting crystal 21 is electrically coupled to the bandpass filter network 50 by shielded cable 51, and the receiving crystal 22 is electrically coupled to the amplifier 40 by shielded cable 52. The amplifier 40 is coupled to the bandpass filter network 50 via a line 53. When power is applied to the electronic circuitry by conventional means from a power supply (not shown), and when conditions required for oscillations to occur are met (including the requirement that the liquid whose level or interface with another fluid is to be detected be in the gap 30) an electrical signal is applied to the transmitting crystal 21 to cause the crystal 21 to resonate in its higher-frequency longitudinal mode. An ultrasonic signal is thereby transmitted across the gap 30 to the receiving crystal 22. The receiving crystal 22 thereupon resonates at the same resonant frequency as the transmitting crystal 21, provided that the ultrasonic signal is not too greatly attenuated in crossing the gap 30.

Attenuation of an ultrasonic signal crossing the gap 30 is inversely related to the density of the material or materials in the gap 30. Thus, there is less attenuation of the ultrasonic signal when a liquid entirely fills the gap 30, than when the liquid rises only to a level between the two end arms 21 and 22 within the gap 30. Attenuation is greatest when the liquid level falls below the gap 30. When the power of the ultrasonic signal reaching the receiving crystal 22 is strong enough to cause the crystal 22 to resonate, the crystal 22 thereby generates an electrical signal. A feedback loop comprising the transmitting crystal 21, the receiving crystal 22, the amplifier 40 and the passband filter network 50 attains oscillation whenever attenuation of the signal from the transmitting crystal 21 to the receiving crystal 22 is exceeded by a preselected gain for the amplifier 40. The gain of the amplifier 40 is selected (taking into account such factors as ultrasonic signal attenuation in the liquid to be detected, losses in the electronic components of the feedback loop, and matching losses between the crystals 21 and 22 and the liquid) to insure that the feedback loop remains in oscillation as long as the level of the liquid to be detected (i.e., the interface between the liquid and whatever fluid lies above it) remains within the gap 30. The value of the gain of the amplifier 40, however, is well below that required to maintain the feedback loop in oscillation when the level of the liquid to be detected falls below the gap 30.

The bandpass filter network 50 is connected by an output line 54 to conventional detector and time delay circuitry 60 for detecting the presence of oscillations in the feedback loop. Particular details of such detector and time delay circuitry could readily be devised by a worker of ordinary skill in the art. In U.S. Pat. No. 3,520,186, for example, a silicon diode detector is used to rectify and filter the output from the feedback loop.

The output from the detector and time delay circuitry 60 is fed via output line 61 to a relay driver 62, which in turn produces a signal on line 63 to drive a relay 64 that actuates a servomechanism for controlling the level of the liquid-fluid interface. As shown in the drawing, the contact points of the servomechanism are represented schematically by reference number 65. The relay driver could comprise, for example, conventional bi-stable Schmitt trigger circuitry for sensing the voltage level at the output of the detector and time delay circuitry 60 and for generating a corresponding voltage signal to drive the relay 64.

At normal amplifier gains, an ultrasonic signal of about 500 kilohertz or higher cannot be transmitted through a gaseous medium. At such high frequencies, the ultrasonic signal is greatly attenuated in the gaseous medium, even over short distances. However, an ultrasonic signal of about 500 kilohertz or higher can be readily propogated through liquids. Consequently, a gas-liquid interface can readily be sensed by causing the transmitting crystal 21 to resonate in its longitudinal (or "thickness") mode at a frequency above 500 kilohertz. Frequencies above 1 megahertz are generally preferred in order to minimize "cross-talk" in the crystal support structure 10. The particular frequency used is selected according to the requirements of the particular application, it being noted that higher frequency signals, which are more easily attenuated than lower frequency signals, generally require higher amplifier gains. Indeed, higher frequency signals are used in the detection of a liquid-liquid interface, where it is desirable to accentuate the differences in attenuation between the two liquids, as is discussed in U.S. Pat. No. 3,520,186.

An ultrasonic liquid level sensing system of the type described above provides an input signal to the detector and time delay 60 only when the feedback loop is in oscillation, i.e., when the liquid level lies within the gap 30. Thus, absence of an input signal to the detector and time delay 60 can mean that the liquid level has fallen below the gap 30, but can also mean that the system is malfunctioning. In accordance with the present invention, a method is provided for checking the integrity of an ultrasonic liquid level sensing system as described above (i.e., for testing whether the amplifier 40 is operational; whether the cables 51 and 52 are properly connected to the crystals 21 and 22, respectively, and to the bandpass filter network 50 and the amplifier 40, respectively; and whether the crystals 21 and 22 are properly bonded to the housing structure 10 and are ultrasonically active), without any liquid being present in the gap 30. Thus, according to the present invention, an ultrasonic liquid level sensing system of the type described above can be installed in a liquid storage tank or other liquid receptacle, and can be tested "in place", before the level of the liquid to be detected reaches the gap 30.

The present invention is based upon the experimental discovery that ultrasonic cross-talk through the cross member 13 of the housing structure 10 is typically as much as ten time greater when the transmitting crystal 21 is excited to resonate in its lower-frequency lateral or "radial" mode than in its higher-frequency longitudinal or "thickness" mode. In accordance with the present invention, use is made of the cross-talk effect by allowing the feedback loop to oscillate in the lower-frequency lateral resonant mode during the integrity checking procedure.

In accordance with the present invention, when the integrity of the ultrasonic system is to be checked, the transmitting crystal 21 is caused to resonate in its lateral mode, typically at a frequency in the 100 to 300 kilohertz range. Such low frequency signals are transmitted internally through the cross member 13 to the receiving crystal 22. In order to perform the integrity test, the passband of the bandpass filter network 50 is shifted down in frequency, so that the lower frequency resonant lateral mode of the crystals 21 and 22 lies within the passband. Down-shifting of the passband of the bandpass filter network 50 can be effected by conventional means within the capability of a worker skilled in the art. For example, a high-value inductor could be switched into the bandpass filter network 50 in order to shift the passband down in frequency during the integrity checking procedure.

An integrity test according to the present invention could be accomplished either manually or automatically. For manual testing, an operator would depress a TEST button 70, which would energize a circuit for causing a relay 71 to activate a mechanism (whose input contacts are indicated by reference number 72) for down-shifting the passband of the bandpass filter network 50 and for causing the transmitting crystal 21 to resonate in its low-frequency lateral or "radial" mode. If the system is operational, the feedback loop would thereby be caused to oscillate in the low-frequency lateral resonant mode of the crystals 21 and 22. A signal indicative of such low-frequency oscillation in the feedback loop would be detected by the detector and time delay circuitry 60, which in turn would provide a signal to the relay driver 62. The output from the relay driver 62 might appropriately drive a relay (either a relay 64 as shown in the drawing or some other relay switched into the system for the purpose), which would activate a means providing a visible or audible signal indicating that the system is operational.

For automatic integrity testing of the system, a timer 80 could be provided for periodically initiating short-term integrity tests. Thus, the timer 80 would replace the manually operated TEST button 70, and could initiate tests of, e.g., 50 millisecond duration once every minute. Initiation of an integrity test, whether manually or automatically, would cause the relay 71 to shift the bandpass filter network 50 down in frequency (as by switching a large-value inductor into the network) in order to enable the detector and time delay circuitry 60 to detect the lower-frequency oscillations in the feedback loop. In automatic operation, an auxiliary detector 81 can advantageously be provided to detect the lower-frequency oscillations in the feedback loop and to cause a READY light 82 on a front panel of the system to blink without requiring activation of the relay 64 whose drive circuitry typically has a delay time of about 0.5 seconds.

This invention has been described above in terms of a particular embodiment, which is to be understood as illustrative rather than limiting. The invention is defined by the following claims and their equivalents.

What is claimed is:

1. A method for testing the integrity of an ultrasonic system for sensing a liquid-fluid interface in a container, said system comprising:
   (a) first and second crystals, each of said crystals having a relatively high resonant frequency and a relatively low resonant frequency;
   (b) a support structure with first and second end arms connected by a cross member, said first crystal being bonded to said first end arm and said second crystal being bonded to said second end arm, said first and second crystals being positioned opposite each other across a gap between said first and second end arms in said container;
   (c) means for selectively enabling said first crystal to resonate either at its relatively high resonant frequency or at its relatively low resonant frequency, said relatively high resonant frequency being sufficiently high to cause an ultrasonic signal to be transmitted into said gap without causing appreciable ultrasonic transmission through said cross portion of said support structure, said relatively low resonant frequency being sufficiently low to cause transmission of a detectable ultrasonic signal through said cross member; and
   (d) means for detecting resonance induced in said second crystal due to resonance of said first crystal at either its relatively high resonance frequency or its relatively low resonance frequency;

said testing method comprising the steps of causing said first crystal to resonate at its relatively low resonant frequency irrespective of whether the liquid-fluid interface lies within said gap in order to cause ultrasonic transmission through said cross member, and detecting resonance in said second crystal at said relatively low resonant frequency, thereby indicating that the ultrasonic system is operational.

2. The method of claim 1 wherein said step of detecting resonance in said second crystal involves causing a feedback loop that includes said first and second crystals to oscillate, and detecting said oscillation in said feedback loop at said relatively low resonant frequency.

3. The method of claim 2 wherein said step of detecting resonance in said second crystal further involves shifting a passband of a bandpass filter in said feedback loop in order to enable said feedback loop to oscillate at said relatively low resonant frequency.

4. The method of claim 3 wherein said step of causing said first crystal to resonate at its relatively low resonant frequency involves causing said first crystal to resonate in a lateral mode generally transverse to a direct path from said first crystal to said second crystal across said gap.

5. An ultrasonic system for sensing a liquid-fluid interface in a container, said system comprising:
(a) first and second crystals, each of said crystals having a relatively high resonant freqency and a relatively low resonant frequency;
(b) a support structure to which said first and second crystals are bonded, said support structure being configured so that said first and second crystals are positioned opposite each other across a gap in said container;
(c) amplifier means and bandpass filter means connected to said first and second crystals so as to form a feedback loop;
(d) means for exciting said first crystal to resonate selectively at said high and low resonant frequencies, said high frequency being sufficiently high to cause an ultrasonic signal to be transmitted across said gap without causing appreciable ultrasonic transmission through said support structure to said second crystal when said liquid-fluid interface lies within said gap, said low frequency being sufficiently low to cause appreciable ultrasonic transmission to said second crystal through said support structure;
(e) switching means for causing said first crystal to resonate at said high frequency and for establishing an operating passband for said bandpass filter means to enable high-frequency oscillations to occur in said feedback loop when said liquid-fluid interface lies within said gap, and means coacting with said switching means for causing said first crystal to resonate at said low frequency and for establishing a testing passband for said bandpass filter means to enable low-frequency oscillations to occur in said feedback loop when said liquid-fluid interface does not lie within said gap, thereby indicating that the integrity of the ultrasonic system is operational.

6. The system of claim 5 wherein said support structure is of generally C-shaped configuration with first and second end arms connected by a cross portion, said first crystal being bonded to said first end arm and said second crystal being bonded to said second end arm, said gap lying between said first and second end arms.

7. The system of claim 6 further comprising detector means for sensing oscillations in said feedback loop.

8. The system of claim 7 further comprising means responsive to said detector means for actuating a servomechanism when oscillations are maintained in said feedback loop due to resonance of said first crystal at said high resonant frequency.

9. The system of claim 8 further comprising integrity test indicative means responsive to said detector means when oscillations are maintained in said feedback loop due to resonance of said first crystal at said low resonant frequency.

10. The system of claim 8 further comprising means for automatically causing periodic oscillations of a selected time duration in said feedback loop at said low frequency.

* * * * *